United States Patent [19]

Dragan

[11] Patent Number: 4,619,613
[45] Date of Patent: Oct. 28, 1986

[54] BULK DENTAL SYRINGE

[76] Inventor: William B. Dragan, 85 Burr St., Easton, Conn. 06612

[21] Appl. No.: 588,290

[22] Filed: Mar. 12, 1984

Related U.S. Application Data

[63] Continuation-in-part of Ser. No. 388,649, Jun. 15, 1982, Pat. No. 4,492,576.

[51] Int. Cl.[4] .................................................. A61C 5/04
[52] U.S. Cl. ........................................ 433/90; 222/575
[58] Field of Search ................... 433/90, 89, 80, 81; 222/461, 460, 570, 569, 567, 575, 326

[56] References Cited

U.S. PATENT DOCUMENTS

| | | | |
|---|---|---|---|
| 742,446 | 10/1903 | Kelly | 433/90 |
| 2,530,999 | 11/1950 | Schuler | 222/567 |
| 2,928,533 | 3/1960 | Loucony | 222/575 |
| 3,285,256 | 11/1966 | Despard | 222/575 |
| 3,724,077 | 4/1973 | Preston et al. | 433/90 |
| 3,827,147 | 8/1974 | Condon | 433/90 |
| 3,854,209 | 12/1974 | Franklin et al. | 433/90 |
| 3,943,628 | 3/1976 | Kronman et al. | 433/89 |

FOREIGN PATENT DOCUMENTS 253651 6/1927 Italy ........................................ 222/575

Primary Examiner—John J. Wilson
Attorney, Agent, or Firm—Arthur T. Fattibene

[57] ABSTRACT

A bulk dental syringe for dispensing predetermined incremental amounts of dental material that includes a barrel assembly that contains a bulk supply of dental material. The barrel assembly is detachably connected to a handle or holder which may be either a finger holder or a lever actuated holder. The barrel assembly is sealed at one end with a displaceable plug or piston, which is engaged by a plunger to express the material therefrom. A discharge spout and a plurality of flexible fingers circumscribing the spout is connected to the other end of the barrel assembly, and a disposable nozzle tip is releaseably secured to the spout by the flexible fingers. A lock collar is provided to positively maintain the flexibe fingers in securement about the nozzle tip. To prevent drooling of the material, a pressure relief arrangement is provided on the end of the plunger.

23 Claims, 19 Drawing Figures

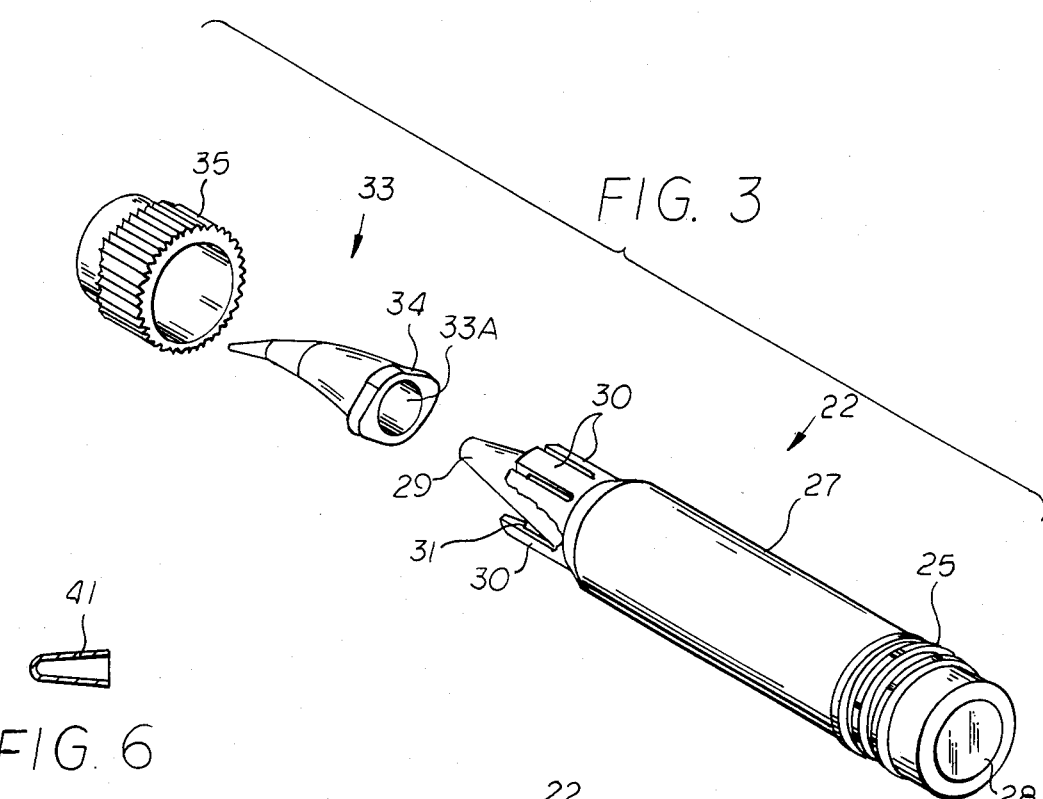
FIG. 3
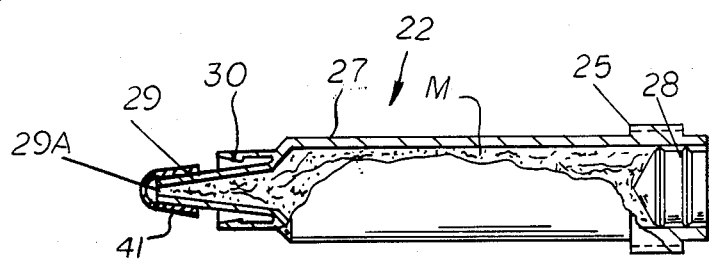
FIG. 6
FIG. 7
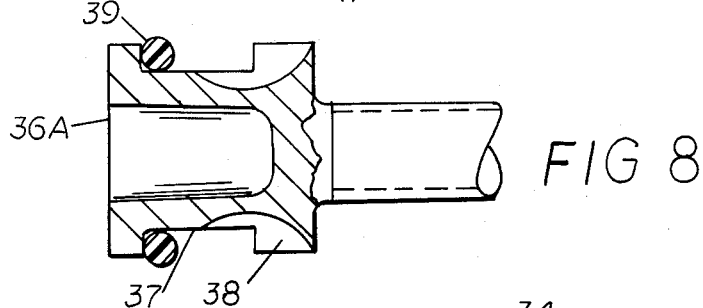
FIG 8
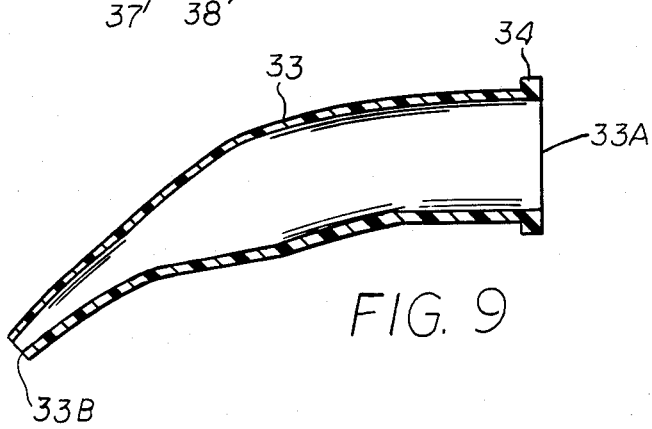
FIG. 9
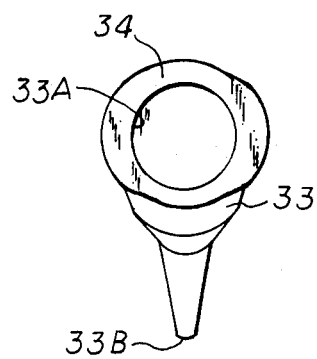
FIG. 10

BULK DENTAL SYRINGE

This application is a continuation in part application, Ser. No. 388,649, filed June 15, 1982, for Dental Syringe and Method of Packaging and Dispensing Dental Material, now U.S. Pat. No. 4,492,576, issued 01/08/85.

FIELD OF INVENTION

This invention relates to dental syringes, and more particularly to a dental syringe for containing a bulk supply of dental material from which the material can be incrementally dispensed directly to a patient's tooth in a manner whereby the hygienic and sanitary integrity of the system can be maintained from patient to patient; and which system provides a means whereby the dental material can be packaged in a container which becomes the barrel portion of a syringe for direct application to the patient.

RELATED APPLICATION

This application relates in part to dental syringes of a type disclosed in my application Ser. No. 314,768 filed Oct. 26, 1981, for All Purpose Dental Syringe, now U.S. Pat. No. 4,472,141.

PROBLEM AND PRIOR ART

This invention relates to improvements in dental syringes of a type for expressing a dental filling material. As disclosed in my prior patents, viz. U.S. Pat. Nos. 3,581,399; 3,900,954; 4,198,756 and design patent U.S. Pat. No. Des. 224,655, a dental material, e.g. a light activating filling material, impression material, temporary filling material, etching gel or sealant and the like, was pre-loaded into a nozzle tip for an individual application and expressed therefrom by a syringe in or onto a tooth. As the structure and techniques disclosed in my foregoing patents have gained acceptance in the dental art, other U.S. patents directed to such structure and technique have been granted. Such subsequent known patents are U.S. Pat. Nos. 4,295,828; 4,330,280; 4,384,853 and 4,391,590.

In each of the foregoing noted patents, the dental material was required to be loaded or preloaded in a nozzle tip or compule in limited amounts. When such nozzle tips are individually loaded by the dentist, it required the dentist to transfer the dental material from a bulk supply, e.g. a jar or other container, in which such material is sold to the nozzle tip. Where such material comprised a light curable material, extreme care had to be exercised in such loading operation to prevent ambient light from setting up the material before it could be applied to the patient. If such nozzle tips or compules were preloaded by the material manufacturer, the quantity of material was generally limited to an individual application or procedure.

Another problem which was recognized was that the application of a dental material from a bulk supply container directly to a patient's tooth was not heretofore feasible because such bulk supply containers lack the dispensing tip and/or attachment therefor, necessary to effect the precise placement of the material directly to the patient's tooth from such bulk container. Also lacking was the concept of a direct dispensing technique whereby the hygienic and sanitary conditions or integrity of the system could be satisfied by the use of a common container on different patients.

OBJECTS

It is therefore an object of this invention to provide a syringe construction for containing a relatively large bulk supply of a predetermined dental material, whereby predetermined amounts of material incrementally can be expressed directly from the bulk supply contained within the syringe to the tooth in the amounts required, and thereby eliminate the intermediate tip loading operation heretofore required by the dentist.

Another object is to incorporate in the syringe a pressure relief means to relieve the pressure acting on the material so as to prevent drooling of the material subsequent to an expressing operation.

Another object is to provide a disposable nozzle tip on the end of the syringe barrel for facilitating the placement of the material to the tooth and for maintaining the hygienic integrity of the instrument for use with different patients.

Another object is to provide an improved syringe barrel construction having a novel gripping arrangement for detachably securing a disposable nozzle tip thereto.

Another object is to provide a syringe barrel construction to which a nozzle tip is detachably secured and which is rendered readily rotatably adjustable through a rotation of 360°.

Another object is to provide a syringe barrel assembly which is constructed to function as a container in which a dental material can be sold in bulk.

Another object is to provide a syringe barrel with a disposable nozzle tip which is detachably secured in a manner to resist separation of the tip from the barrel during an extruding operation, and yet be removed and replaced with a minimal effort.

SUMMARY OF THE INVENTION

The foregoing objects and other features and advantages are attained by a dental syringe construction having a barrel assembly arranged to contain a bulk supply of a predetermined dental material, and from which the dental material can be incrementally expressed as required directly to the tooth from the syringe bulk supply. The barrel assembly is detachably secured to a holder, which may be a finger grip or guard type holder, or a lever actuated holder.

The barrel assembly comprises an elongated tubular member which is opened at one end and which is sealed by a piston or plug. On the other end thereof, there is formed a dispensing spout. Circumferentially spaced about the spout are a plurality of flexible fingers which are undercut or formed with a notch. A disposable tip defining a nozzle is detachably secured for relative rotation about the spout by the fingers. To facilitate detachment and to effect a positive lock, the nozzle tip is provided with a laterally extending flange which is non-circular or eliptical so that the respective fingers grip the flange to a varying degree. A lock collar is fitted over the fingers to positively bias the fingers into gripping position onto the nozzle flange. The arrangement is such that the nozzle tip is positively secured to the barrel so that separation is prohibited during an extruding operation, and whereby the removal of the nozzle tip can be effected with minimal force upon the freeing of the collar from the fingers.

Displacement of the piston or plug is effected by a plunger. In accordance with this invention, the plunger is provided with an arrangement which will automtically relieve any back pressure created during an extruding operation to prevent drooling of the material when the pressure on the plunger is released. This is attained by providing an annular groove on the end of the plunger adjacent the plug and providing the groove with a vent slot which is sealed between an open and closed position by a sealing member as the plunger is reciprocated within the barrel for expressing the material therefrom as desired. An end cap is provided for sealing the spout when the syringe is not in use.

FEATURES

A feature of this invention resides in a syringe construction having a readily detachable barrel assembly and which barrel assembly forms the container for a bulk supply of dental material.

Another feature resides in the provision of a disposable nozzle tip which is detachably connected to the barrel in a manner to prohibit separation during a dispensing operation, and which is rendered readily removable by the application of a minimal pull.

Another feature resides in the provision whereby the nozzle tip is adjustably secured for rotation of 360° relative to the barrel.

Another feature resides in providing the barrel assembly with a plurality of flexible fingers for releasably connecting the nozzle tip to the barrel.

Another feature resides in a plunger having a pressure relief means formed on the end thereof for automatically relieving the back pressure created during an extruding operation to effectively eliminate drooling.

Other features and advantages will become more readily apparent when considered in view of the following detailed description and drawings in which:

FIG. 3 is an exploded prospective view of a barrel assembly for use in the syringe construction of FIG. 1 and FIG. 2.

FIG. 6 is a detail view of an end cap.

FIG. 7 illustrates the barrel assembly used as a container for the bulk supply of dental material.

FIG. 8 is an enlarged detail of the pressure relief means on the end of the plunger.

FIG. 9 is a detail side view of the nozzle tip, having parts in section.

FIG. 10 is an end view of the nozzle tip.

DETAILED DESCRIPTION

Figure 1:
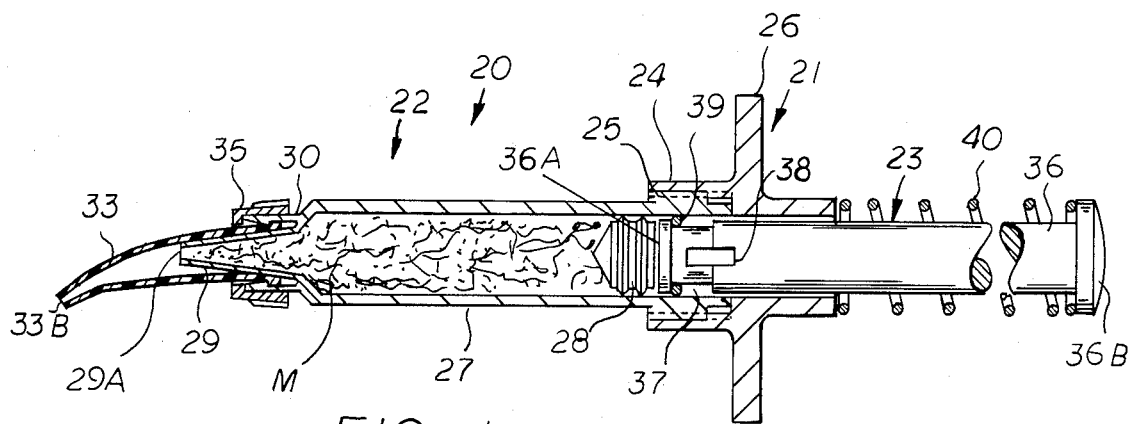
FIG. 1 is a sectional side view of a syringe construction embodying the invention.

Referring to the drawings, there is shown therein syringe construction 20 and 50 which embody the invention. The construction of syringe 20 comprises a holder 21, a barrel assembly 22 and a plunger means 23. As shown, the holder 21 comprises a hub 24 which is internally threaded for detachably receiving the barrel assembly 22, which is externally threaded at 25 as best seen in FIG. 3. Circumscribing the hub 24 is a finger grip 26.

Figure 4:
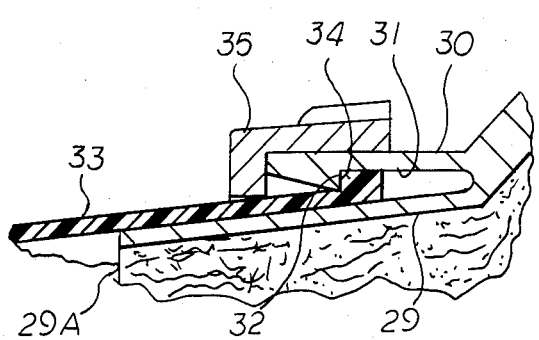
FIG. 4 is a fragmentary enlarged section view showing the finger portion of the barrel assembly.
Figure 5:
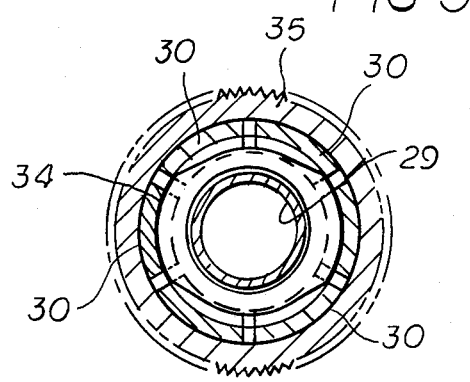
FIG. 5 is an enlarged sectional view taken along line 5—5 on FIG. 2.

In accordance with this invention, the barrel assembly 22 comprises an elongated tubular member 27 which is filled with a bulk supply of a dental filling material, M, such as a light activated composite, an impression material, an etching material, a temporary filling material or the like. It will be understood that the tubular member 27 may be formed of an opaque or light impervious material when used with a light activated composite. One end of the tubular member is provided with a full opening that is sealed by a piston or plug 28 which is displaceable along the tubular member 27 by the plunger means 23 as will be hereinafter set forth. The other end of the barrel or tubular member is formed with a discharge spout 29. In the illustrated embodiment, the spout 29 is tapered toward its end opening 29A. Circumferentially spaced about the spout 29 are a plurality of spaced flexible fingers 30. As best seen in FIG. 4, each finger 30 is provided with an undercut or notch 31 which defines a lip 32 arranged to snap over and retain a nozzle tip 33 as will be hereinafter described.

Referring to FIGS. 1, 2, 3 and 5, the nozzle tip 33 is provided with an inlet end 33A which is circumscribed by a flange 34. In accordance with this invention, the flange 34 is non-circular or elliptical in shape, so that the flange 34 projects laterally a varying amount. The arrangement is such that when the nozzle tip 33 is fitted over the spout 29, the lip 32 of the respective fingers 30 will snap over the flange 34 so that the restraining force exerted by the lip 32 on the flange will vary in accordance with the progressive lateral extension of the corresponding flange portion.

To positively retain the fingers 30 in latching position on the flange 34 of the nozzle tip, a locking collar 35 is provided. The lock collar 35 comprises an annular member arranged to frictionally slide over the fingers 30, and in the assembled position as shown in FIG. 4, maintain the respective fingers latched onto the nozzle tip 33.

Slidably disposed within the barrel assembly is a plunger means 23. The plunger means comprises a plunger shaft 36 having a head end 36B and a front end 36A arranged to engage the end of the plug 28. Adjacent the front end of the plunger shaft 36, there is provided a pressure relief means in the form of an annular groove 37. Disposed in communication with the groove 37 is a vent slot 38. As best seen in FIG. 8, the vent slot 38 communicates with the rear portion of the groove only. Displaceably disposed within the groove 37 is a sealing member in the form of an O-ring 39. A spring 40 is disposed on the plunger shaft 36, which bears on the end of the hub 24 and the end 36B of the plunger means. Thus, the spring 40 normally biases the plunger means toward its normal protracted position.

To seal the spout when the syringe 20 is not in use, an end cap 41 is fitted over the spout opening 29A.

To dispense the material M from its bulk supply, i.e. from the tubular member, the lock collar 35 is removed from the flexible fingers and a disposable nozzle tip 33 is fitted over the spout 29 until the lip 32 of the fingers 30 snap fit over the tip flange 34. The collar is then slipped onto the fingers whereby the collar retains the fingers in positive gripping position onto the nozzle flange 34 as hereinbefore described. The arrangement is such that with the collar in locking position, the nozzle tip can be rotated a full 360° to direct the discharge opening 33B thereof in any desired direction. Positive securement of the nozzle tip to the spout by the fingers is essential in order to prohibit the nozzle tip from separating from the spout during an extruding operation. This is particularly necessary as the dental material is generally very heavy or viscous, resulting in a considerable pressure being imposed on the nozzle tip during a dispensing operation.

It will be noted that as the plunger shaft 36 is pushed against the force of the spring 40 to displace the plug 28 and express a corresponding amount of material M, the sealing ring 39 is displaced to the rear end of the groove 37 so that the vent slot 30 is open to effect evacuation of air. Upon the return of the plunger shaft by the bias of spring 40 acting thereon upon completion of an extruding stroke, the sealing ring 40 is shifted toward the end 36A of the plunger shaft, thus sealing closed the vent slot 3B and creating a vacuum on the back end of the plug 28. The creation of the vacuum on the back end of the plug is sufficient to effect a slight backward movement of the plug to relieve any build-up of pressure on the material, thus preventing the drooling of the material after an extruding stroke.

To remove the used nozzle tip 33, the lock collar 35 is removed from the fingers to free the same. In this position, the flange 34 of the nozzle tip can be readily freed from the fingers by imparting a slight pull thereto. The force or pull necessitating separation is reduced to a minimal force because of the varying degree of overlap between the lip 32 of the respective fingers and the progressively diminishing flange 34.

As noted in FIG. 7, the barrel assembly may comprise a container in which the material M can be packaged and distributed in bulk by a material manufacturer or which can be loaded by the dentist if so desired. With the material so loaded, the syringe barrel assembly can be readily threaded to the syringe holder 21 which includes the plunger means 23 assembled thereto. As herein described, the nozzle tip is then fitted over the spout and secured thereto.

Figure 2:
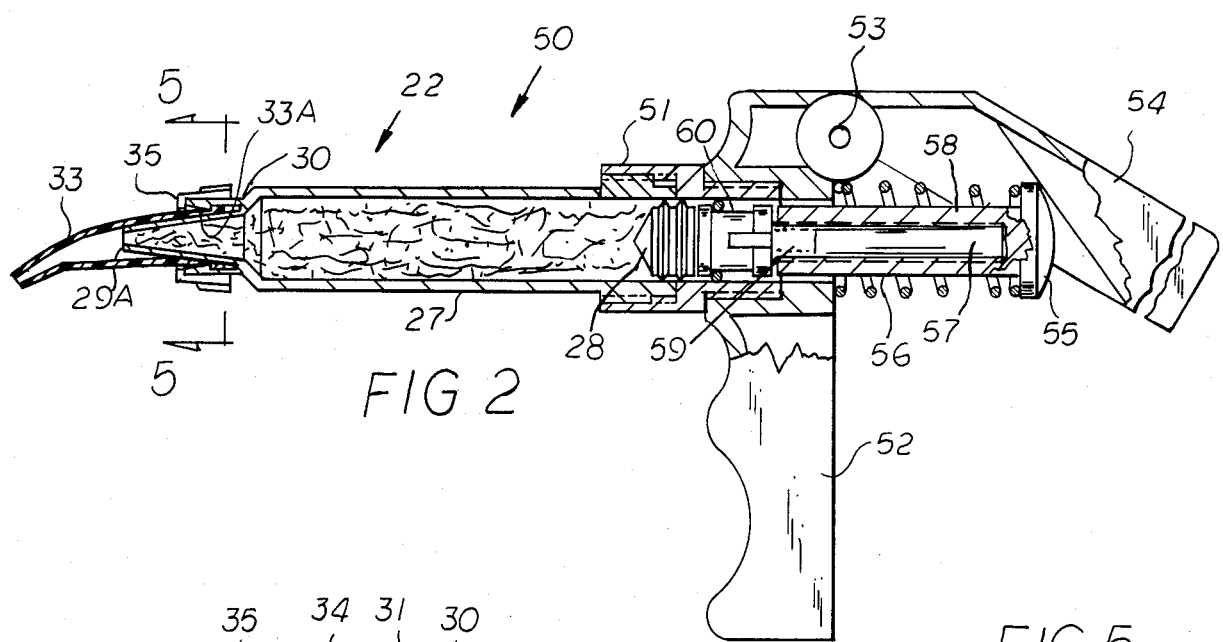
FIG. 2 is a sectional view of a modified syringe construction.

FIG. 2 illustrates a modified embodiment. This form of the invention differs from that described in that the holder 51 is connected to a fixed handle member 52 that extends normal thereto. Pivotably connected about a pivot 53 is an actuating lever 54 arranged to bear on the head end 55 of the plunger means 56. Thus, the displacement of the plunger means 56 is effected by pivoting the lever 54 toward the fixed handle member 52 by a squeezing action. A spring 57 disposed about the plunger means 56 exerts a spring bias on the plunger means 56.

In the illustrated embodiment, the plunger means 56 comprises a pair of telescoping members 57 and 58. The outer member 58 comprises a hollow sleeve having a threaded bushing 59 for receiving a thread shank 57 which defines the inner member. With the arrangement described, the length of the plunger means 56 can be extended as the material in the barrel is depleated by adjusting the outer sleeve 58 relative the inner member 57. The inner end of the inner member is provided with a pressure relief means 60 which is similar to that hereinbefore described. The barrel assembly 28 of syringe 50 is similar in all respects to the barrel assembly of FIGS. 1 and 3 to 7 as hereinbefore described.

From the foregoing, it will be apparent that the barrel assembly 28 of FIG. 7 can be used with a holder 21 of FIG. 1 or with a power handle or holder 51 of FIG. 2.

It will be understood that the tubular member or barrel 27 may be sized to contain any predetermined convenient bulk supply of material. For example, 5 cc of a suitable dental material may be a convenient amount. It will be understood, however, that the barrel may be sized to contain more or less as may be deemed to be a practical barrel supply. With the embodiment disclosed in FIG. 1, the amount of material which can be dispensed during any procedure can vary from a nominal amount, e.g. 0.1 cc to the entire contents of the barrel, depending upon how far the plunger 23 is advance by the dentist.

With the embodiment of FIG. 7, the dentist can adjust the amount of material dispensed upon a single squeeze of the handle 52 and lever 54 by first effecting the adjustment of the plunger segments or sections 57 and 58 relative to one another. Thus, the adjustment of the plunger sections 57 and 58 determines the amount of material dispensed.

Another feature resides in that the sealing cap 41 used to seal the end of the spout 29 may be color coded to the color of the dental material, where for example varying shades of a light activated composite material is packaged in any given tubular barrel. With the sealing cap color colded to a particular shade of material, a dentist can readily determine what color shade of material is contained in a given tubular barrel 27.

Figure 17:
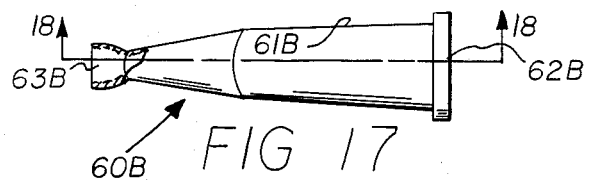
FIG. 17 is a plan view of another modified nozzle tip construction having portions broken away.
Figure 18:
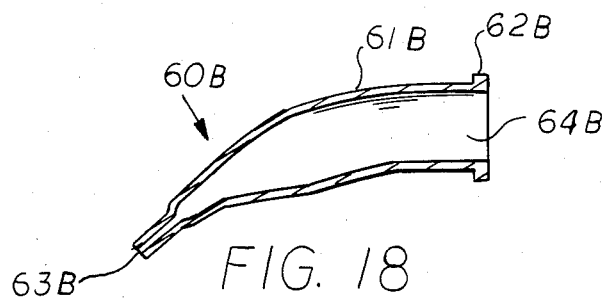
FIG. 18 is a section view taken on line 18—18 on FIG. 17.
Figure 19:
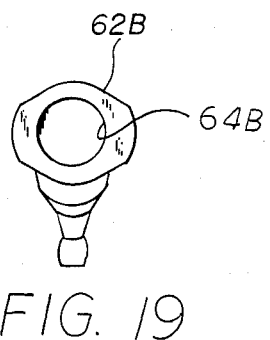
FIG. 19 is an inlet end view of FIG. 17.

FIGS. 17, 18 and 19 illustrate a modified nozzle tip construction 60B which may be used with the syringe construction of FIGS. 1 or 2. Where the nozzle tip construction 33, hereinbefore described, is provided with a discharge orifice 33B, at the discharge end which is circular in cross-section, to function for extruding the dental material in a fine "thread-like" configuration, the nozzle tip 60B is provided with a discharge orifice configuration at the discharge end which is generally flat as indicated at 63B so that the dental material is extruded therefrom in the shape of a flat ribbon. For certain dental procedures, e.g., in an etching and/or sealing procedure, a flat broad, brush-like shape extrudant is desirable. As hereinbefore described, the inlet end 64B is circumscribed by a laterally extending flange 62B which is non-circular, and which will function like flange 34 of nozzle tip 33 so that nozzle tip 60B can be positively secured by fingers 30 of the syringe barrel 27, and yet be rendered readily releasable by a slight pull due to the eccentricity of the flange 62B; as hereinbefore described.

Figure 11:
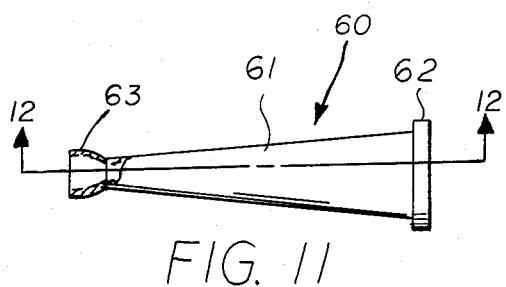
FIG. 11 is a detailed plan view of a modified nozzle tip construction, having portions broken away.
Figure 12:
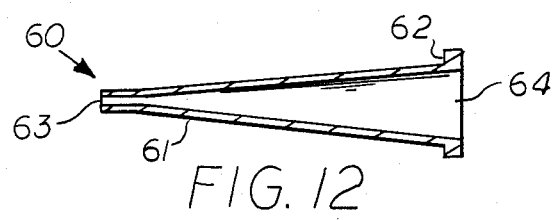
FIG. 12 is a section view taken on line 12—12 of FIG. 11.
Figure 13:
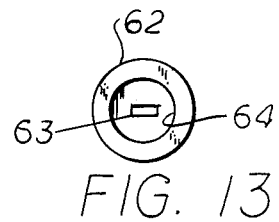
FIG. 13 is an inlet end view of FIG. 11.

FIGS. 11 to 13 illustrate another modified nozzle tip construction 60. In this form of the invention, the nozzle tip 60 is generally straight to define a funnel shape longitudinally extending chamber through which the extrudent dental material flows from an enlarged inlet end 64 to the discharge orifice 63. As best seen in FIGS. 11 and 13, the discharge orifice is flattened to define a generally rectangular opening whereby the dental material can be extruded as a flat ribbon. As shown, the walls of the tip 60 taper or converge from the inlet end 64 to the discharge end 63. In this form, the end flange 62 is illustrated as being circular. However, when the nozzle tip 60 is intended to be used with a syringe construction as described with FIGS. 1 and 2, the flange 62 should be non-circular as described with respect to nozzle tip 33 or nozzle tip 60B. The nozzle tip 60 having the circular flange 62 can be utilized with the prior art syringe construction of my prior noted patents when a "broad-flat ribbon like extrudent" is desirable.

Figure 14:
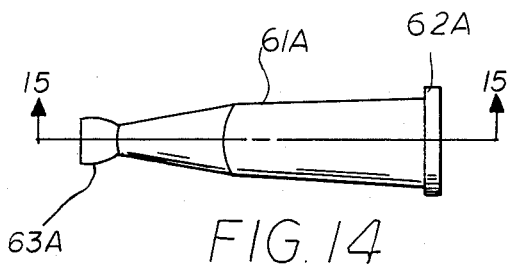
FIG. 14 is a plan view of a modified nozzle tip construction.
Figure 15:
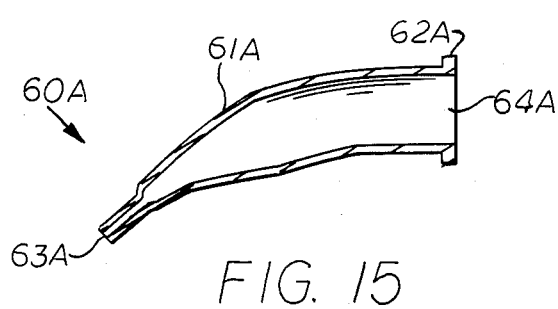
FIG. 15 is a section view taken on line 15—15 of FIG. 14.
Figure 16:
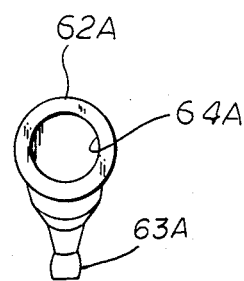
FIG. 16 is an inlet end view of FIG. 14.

FIGS. 14 to 16 illustrate a modified nozzle tip 60A which is similar to that of FIGS. 11 to 13, but differs therefrom in that the nozzle tip is provided with an offset or angular disposed discharge orifice 63A; which is flattened as hereinbefore described. The reservoir or chamber 61A is somewhat arcuate, and which shape facilitates access to the posterior, difficult to reach, teeth. In FIGS. 14 to 16, the flange 62A is illustrated as being circular; however, it will be understood that for use with syringe barrel 22 as herein described, the flange 62A should be configured as described with respect to nozzle tips 60B and 33.

It will be understood that the various nozzle tips herein disclosed are formed of a relatively inexpensive plastic material that will render them readily expendible after use, and also which may be either transparent or opaque to light, the opaque tip being rendered more suitable for use in the application of light curative restorative and/or dental materials. As shown, the body or chamber portion of the respective nozzle tips may be formed so as to provide an angularly off-set discharge orifice, e.g. FIGS. 14–19 or with a co-axially disposed discharge orifice, e.g. the nozzle tip of FIGS. 11 to 13. Also, the end flange may be either circular or non-circular, as herein described; the non-circular flange being preferred when used in conjunction with the barrel assembly 22 as herein described.

While the invention has been described with respect to several embodiments thereof, variations and modifications may be made without departing from the spirit or scope of the invention.

What is claimed is:

1. A dental syringe for dispensing a predetermined amount of dental material directly to a tooth from a bulk supply of said material comprising
   a barrel means defining an elongated tubular member adapted to contain a bulk supply of a dental material,
   a discharge spout formed on one end of said tubular member,
   said tubular member being opened at its other end,
   a plug sealing said opened end to confine a material within said tubular member,
   means defining a plurality of flexible fingers connected to said tubular member, said fingers circumscribing said discharge spout,
   said fingers having an internal retaining notch,
   a nozzle tip detachably connected to said spout,
   said tip having a laterally extending flange adjacent one end and a nozzle orifice formed at its other end,
   said nozzle tip being fitted over said spout whereby said flange is engaged by said finger retaining notch for detachably retaining said nozzle tip on said spout,
   and a collar slidably disposed relative to said fingers for positively securing said fingers in gripping relationship onto said nozzle tip,
   a plunger slidably mounted within said tubular member for engaging said plug for extruding the dental material through said point and associated tip as said plug is displaced.

2. A dental syringe as defined in claim 1 and including means operatively connected to said plunger to prohibit drooling of the material from said tubular member upon release of the pressure imparted by said plunger to said plug.

3. A dental syringe as defined in claim 1 wherein said flange circumscribes said one end of said nozzle tip.

4. A dental syringe as defined in claim 1 wherein said laterally extending flange is non-circular.

5. A dental syringe as defined in claim 1 wherein said flange extends laterally a progressively varying amount whereby the retention force of said fingers acting on said nozzle tip varies accordingly.

6. A dental syringe for incrementally dispensing a predetermined amount of material from a bulk supply directly to a tooth comprising
   a tubular barrel means adapted to contain a bulk supply of dental material,
   a spout formed on one end of said barrel,
   a plurality of flexible fingers circumscribing said spout,
   a detachable nozzle tip fitted on said spout,
   means for positively securing said nozzle tip to said spout to prohibit said nozzle tip from becoming separated from said spout during the extruding of said material from said barrel means,
   and a plunger means slidably mounted in said barrel for expressing said material therefrom by displacement of said plunger means relative to said barrel means.

7. A dental syringe as defined in claim 6 whereby said plunger means includes a means for relieving the back pressure on the material upon release of the pressure acting on said plunger means.

8. A dental syringe for incrementally dispensing a predetermined amount of material from a bulk supply directly from said bulk supply to a tooth comprising
   a means defining a holder,
   an elongated barrel,
   means for detachably connecting said barrel to said holder,
   said barrel including an elongated tubular member,
   said tubular member being opened at one end,
   a displaceable plug sealing said open end,
   and a spout connected to the other end of said tubular member,
   a plurality of flexible fingers connected to said other end of said tubular member,
   said fingers being circumferentially spaced about said spout,
   a disposable nozzle tip adapted to be detachably connected to said spout,
   complementary means formed on said fingers and said nozzle tip for securing said tip,
   and a plunger means slidably disposed in said barrel for effecting incremental displacement of said plug.

9. A dental syringe as defined in claim 8 wherein said holder means comprises
   a hub for detachably receiving said barrel,
   and a finger grip circumscribing said hub,
   and a spring means for normally biasing said plunger toward its normal inoperative position.

10. A dental syringe as defined in claim 9 and including means in said plunger for relieving the back pressure of said material to prohibit drooling of said material.

11. A dental syringe as defined in claim 10 wherein said means includes an annular groove formed in said plunger adjacent the end thereof, a vent slot communicating with said groove, and a sealing ring displaceably mounted in said groove for valving said vent slot between an opened position during an extruding stroke of said plunger and a closed position on the return stroke of said plunger.

12. A dental syringe as defined in claim 8 wherein said holder means comprises a hub for detachably receiving said barrel on one end thereof, a fixed handle member connected to the other end of said hub, and an actuating lever means pivotably connected to said fixed handle member, said lever means bearing on the end of said plunger whereby said plunger is displaced toward said barrel as said lever means is actuated, and a spring means for normally biasing said plunger means toward said lever means.

13. A dental syringe as defined in claim 12 wherein said plunger means comprises a pair of telescoping members, and said telescoping members having complementary means for effecting the extension and retraction thereof relative to one another.

14. A dental syringe as defined in claim 13 and including a pressure relief means adjacent one end of one of said telescoping members, said pressure relief means including an annular groove, a vent slot in communication with said groove, and a sealing ring displaceably disposed in said groove for valving said vent slot between open and closed position as said plunger means reciprocates within said barrel during a dispensing operation.

15. A dispensing syringe barrel for containing a bulk supply of dental material comprising an elongated tubular member which is opened at one end, said tubular member defining a reservoir for containing a bulk supply of material, a spout connected to the other end of said tubular member, a displaceable plug sealing said open end, a plurality of flexible fingers connected to the other end of said tubular member, said fingers being circumferentially spaced about said spout, a disposable nozzle tip fitted to said spout, and means for positively securing said nozzle tip to prohibit separation of said tip from said spout during a dispensing operation.

16. A dispensing syringe barrel as defined in claim 15 and including connecting means formed adjacent the open end of said tubular member adapted for connecting said tubular member to a holder.

17. A dispensing syringe barrel as defined in claim 15 wherein said fingers are integrally formed from the material of said tubular member.

18. A dispensing syringe barrel as defined in claim 15 wherein said last mentioned means include a notch formed on said fingers, and said nozzle tip having a laterally extending flange adapted to be releaseably retained by said finger notch.

19. A dispensing syringe barrel as defined in claim 18 wherein said flange extends laterally a progressively varying amount whereby said finger notches variably grip said flange.

20. A dispensing syringe barrel as defined in claim 19 and including a lock collar fitted onto said fingers for biasing said fingers into locking relationship with said tip flange.

21. A dispensing syringe barrel as defined in claim 20 and including an end cap for sealing said spout.

22. A dispensing syringe barrel for containing a bulk supply of dental material comprising an elongated tubular member which is open at one end, said tubular member defining a reservoir for containing a bulk supply of material, a spout connected to the other end of said tubular member, a displaceable plug for sealing said open end, and a plurality of flexible fingers connected to the other end of said tubular member, said fingers being circumferentially spaced about said spout.

23. A dispensing barrel as defined in claim 22, and including a sealing cap for sealing the end of said spout.

* * * * *